United States Patent
Vinas

[19]

[11] Patent Number: 6,062,688
[45] Date of Patent: May 16, 2000

[54] DETACHABLE EYEGLASS FOAM SHIELD

[76] Inventor: Joseph F. Vinas, 502 Oakland Hills, Kerrville, Tex. 78028

[21] Appl. No.: 09/128,919

[22] Filed: Aug. 4, 1998

[51] Int. Cl.[7] ...................................................... G02C 9/00
[52] U.S. Cl. ................................................ 351/47; 351/44
[58] Field of Search .................................. 351/47, 48, 57, 351/58, 41, 158, 44; 2/12, 13

[56] References Cited

U.S. PATENT DOCUMENTS

| | | |
|---|---|---|
| Re. 34,512 | 1/1994 | Dowdy et al. . |
| 4,245,630 | 1/1981 | Lloyd et al. . |
| 4,614,183 | 9/1986 | McCracken et al. . |
| 4,781,956 | 11/1988 | Zimmermann et al. . |
| 4,785,481 | 11/1988 | Palmer et al. . |
| 4,837,062 | 6/1989 | Dunshee et al. . |
| 5,019,071 | 5/1991 | Bany et al. . |
| 5,243,711 | 9/1993 | Graham . |
| 5,282,791 | 2/1994 | Lipton et al. . |
| 5,300,963 | 4/1994 | Tanaka . |
| 5,339,119 | 8/1994 | Gardner . |
| 5,388,269 | 2/1995 | Griffin . |
| 5,520,629 | 5/1996 | Heinecke et al. . |
| 5,548,351 | 8/1996 | Hirschman et al. . |
| 5,611,356 | 3/1997 | Rothrum . |
| 5,614,963 | 3/1997 | Parker . |

*Primary Examiner*—Hung Xuan Dang
*Attorney, Agent, or Firm*—Royston, Rayzor, Vickery, Novak & Druce, L.L.P.

[57] ABSTRACT

An eye shielding system is provided that permits a disposable, air-permeable shield to be releasably secured to the frame of eyeglasses or goggles. A shield is provided that encloses the area between the face and the frame. The eyeglasses or goggles retain lenses or an eye shield to prevent debris or contaminants from reaching the eyes, and have a frame, and temple connectors. The frame provides support for the shield. The forward part of the shield is fitted to the rear side of the frame, and is reversibly retained thereby. The shield extends rearwardly, and seals with the face of the wearer. The shield allows air to pass through it in order to inhibit fogging up of the eyeglasses, but resists passage of sprayed liquids or solids, to prevent airborne liquid or solid debris or contaminants, including those contacting the face, from coming into contact with the eyes.

46 Claims, 9 Drawing Sheets

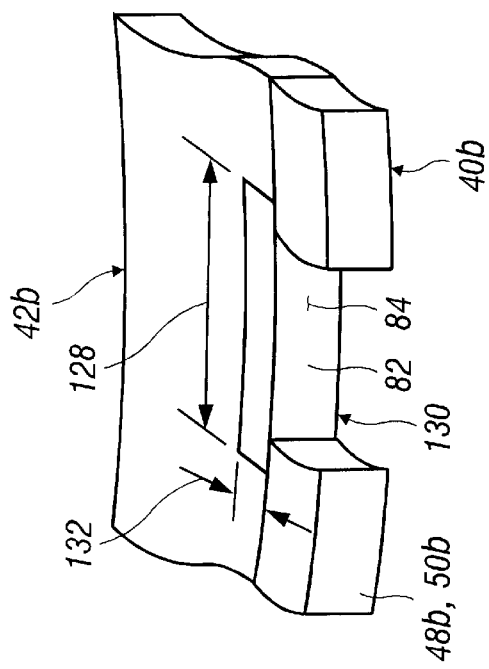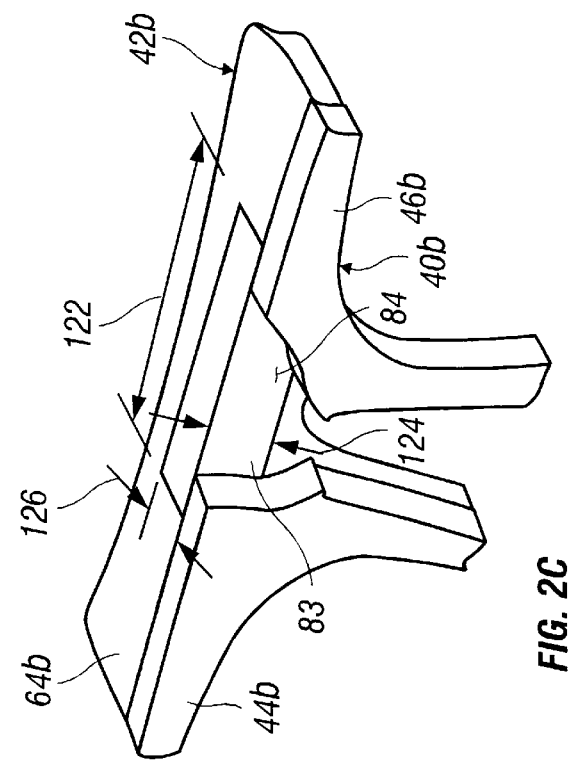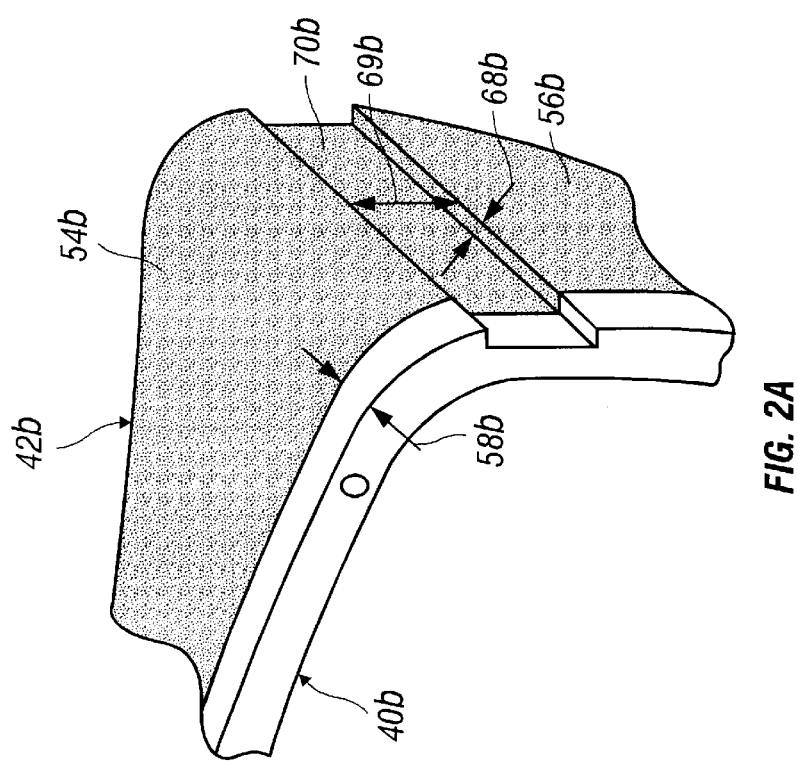

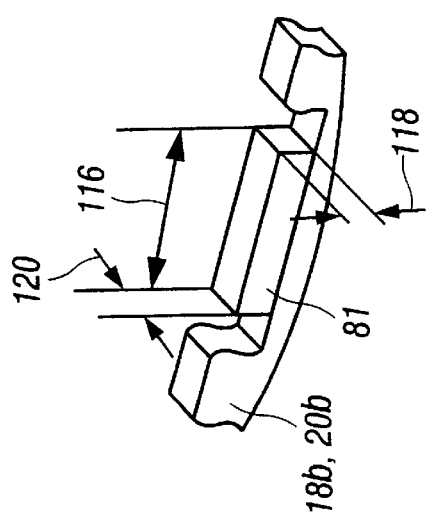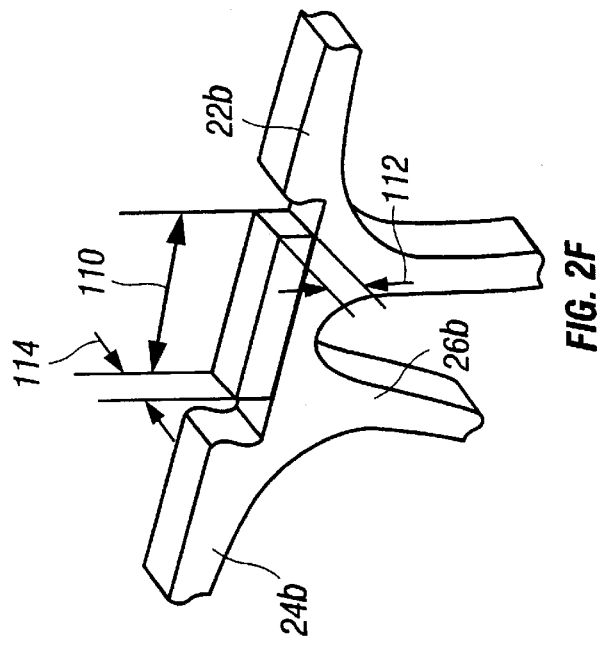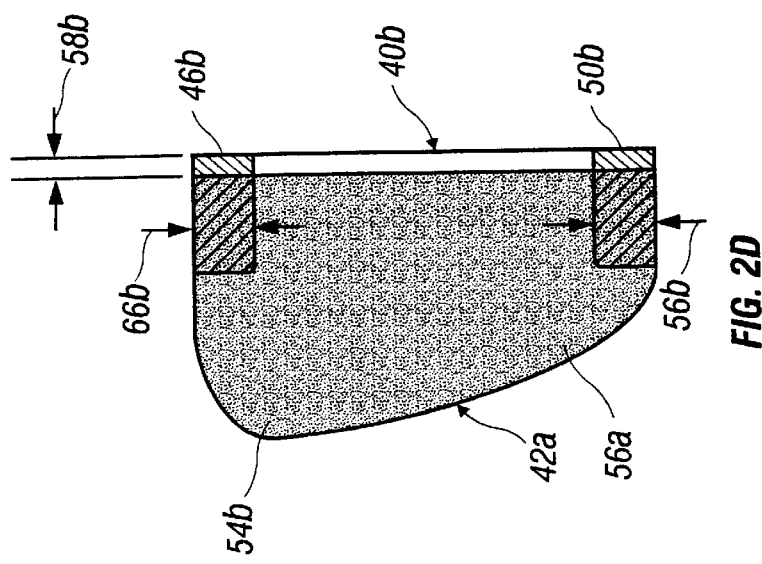

DETACHABLE EYEGLASS FOAM SHIELD

FIELD OF THE INVENTION

The present invention relates to a device usable with eyeglasses or the like having a shield to protect the eyes, for example from liquid or solid matter that is airborne and reaches the face. More particularly it relates such a device in which the shield is detachable from the eyeglasses.

BACKGROUND OF THE INVENTION

The invention relates to an eye shielding system usable with eyeglasses or eye goggles and a detachable foam shield. Other shields meant to protect the eyes from liquids are available, but ones that are usable for personnel that must wear prescription glasses have drawbacks. They may be permanently or non-reversibly attached to glasses, which means that the user must have a second pair of prescription glasses dedicated to the shield, and that the shield and glasses must be sanitized after use. Some shields for wearers of prescription glasses are bulky, can impair the vision of the wearer, and interfere with the operation of the earpieces. Many other shields do not seal or fit snugly against the face, allowing liquids that reach the face above the eyes to drip down the face into the eyes. Shields that seal may not air-permeable, and do not inhibit the insides of the lenses from fogging up.

Previous shields disclosed in patents are understood to include the following:

U.S. Pat. No. 4,785,481 discloses protective eyeglass shields (FIGS. 1 & 2) for use by surgeons to prevent contact with liquid-transmittable contagions, such as the AIDS virus. The flexible shields are preferably air-permeable to prevent fogging of the lenses. The shield pieces are not disclosed as being removable or detachable from the frame, nor are they continuous. The shields attach to both the frame and earpieces of the eyeglasses.

U.S. Pat. No. 5,300,963 shows a protective hood made of soft resin material heat molded to the eyeglasses frame when, during heating, some of the resin material fills grooves in the frame. Thus, the protective hood is not reversibly joined to the frame. The hood is not described as being air-permeable.

U.S. Pat. No. 5,339,119 discloses a protective eyeglass cover made of air-permeable foam, which provides sufficient air circulation to minimize fogging of the lenses. The cover is described as being useful in medical fields to protect the user's eyes from bodily fluids and the like. However, the cover encases and lies outward of the frame, excepting the earpieces which are inserted through apertures in the cover to hold it in place. The cover is held in place by the clamping effect between the earpieces and the head, and by support from the frame.

U.S. Pat. No. 5,548,351 discloses protective eyeglass shields coupled to is eyeglass frames by the engagement of the earpieces with a longitudinally extending channel formed in each shield. The shields are non-reversibly attached to the eyeglasses by the insertion of pin into an opening that locks the shield to the earpiece. The shields are not described as air-permeable, and provide protection only peripherally.

U.S. Pat. No. 5,243,711 discloses an integral shield and lens-piece, where the shield is made of plastic foam, primarily for use during hair styling to protect the wearer from hair spray. The shield is not described as removable.

U.S. Pat. No. 5,388,269 shows a protective eyeglass shield with slots formed in the shields for support from the earpieces of an eyeglasses frame. The shield is not described as air-permeable, and protects only peripherally.

U.S. Pat. No. 5,614,963 shows an eyeglasses shield which is detachably mounted to an eyeglasses frame by posts which engage holes in the eyeglasses frame. It is not described as air-permeable, nor does it fit against the face.

It can be seen that the foregoing do not meet all of the needs of medical or other personnel who must wear prescription lenses and are subject to the risk of harmful substances coming in contact with their eyes. The present invention meets all of these concerns. It is detachable, and may be disposed of after use, fits snugly and seals against the face, protecting against sprayed liquids, and is air-permeable. It is also small, does not interfere with vision or with the fit of the glasses.

This invention is unique because it uses a detachable, air-permeable shield that is attached to the frames of the glasses or goggles, without the necessity of attaching to the earpieces or other connectors holding the eyeglasses to the face, and also because it fits snugly and seals against the face. It is also lightweight and made of low-cost materials, and may thus be disposable.

The shield is designed to fit closely inside the eyeglass or goggle frames and is made of an air-permeable material to inhibit fogging of the lenses. It is particularly useful for providing protection for surgeons or other medical personnel from splashed liquids or solids. It is also useful for any workers who must wear some protective shield for their eyes. It is particularly directed toward protection from splashed bodily fluids or other harmful materials, such as those which may carry diseases such as the AIDS virus or which are otherwise harmful or dangerous. The detachable shield may be attached to either standard, or slightly modified eyeglasses.

SUMMARY OF THE INVENTION

This invention provides a low cost, detachable, air-permeable shield for eyeglasses or eye goggles that does not allow passage of either liquids or solids splashed on it. It provides a sufficiently snug fit or seal between both the shield and the eyeglass frames, and between the shield and the face to adequately protect the eyes from materials splashed onto the face. This invention includes the shield itself, which can take on a number of different variations, and may include a set of eyeglasses or goggles, often with prescription lenses, which may or may not have been modified to accept a shield of this invention.

A first function is that it protect the eyes from splashed liquids or solids, which means that it must fit snugly to both the face and the frame of the eyeglasses or goggles, thus creating a seal to exclude materials on the face in order to provide protection. Another function of this invention is that the shield permit enough air to pass through it, so that it inhibits the fogging up of the wearer's eyeglasses or goggles, which is particularly important as the use envisioned is for medical personnel in either an operating room or an emergency room setting. One desire is that the shield itself be of low cost, which means that it can be disposable, important in use in a medical situation. A further desire is that the system be easy to use and comfortable to wear, which is important because medical personnel may be required to wear them for extended periods of time; it is desirable that they not be bulky or uncomfortable so as to discourage persons from wearing them.

There is nothing in the prior art that meets all of these objectives. The preferred embodiment is constructed primarily of air-permeable foam so that it inhibits fogging of the lenses, and is also lightweight. The materials used in construction are also relatively inexpensive. Nor does the invention require large modifications, or necessarily even any modifications, to the eyeglasses of the wearer, although the eyeglasses may be custom-made so as to promote a snug fit between the frame and the shield. The shield is held onto the eyeglasses by a retainer, or retainers, which may take a number of different forms. The shield is also easily attachable or removable, which is important if the system is meant to be used in a medical environment, where the shield may be required to be disposable. Further, being placed between the face and the eyeglasses, the shield may be smaller and made of less material. Being constructed of foam rubber also permits the shield to be resilient and to mold itself to the contours of the face, thus creating a seal preventing entry into the protected area of either liquids or solids splashed on the face.

The further scope of this invention will become apparent upon the review of the detailed description of the preferred embodiments. It should however be understood that these descriptions do not limit the scope of the invention and are given as examples only, and that various changes and modifications which are fully within the scope of the present invention will become apparent to those skilled in the art.

BRIEF DESCRIPTION OF THE DRAWINGS

The present invention is more easily understood with reference to the drawings, in which:

FIG. 2A is a perspective view of detail of a groove in the shield in FIG. 2.

FIGS. 2B and 2C are partial cutaway perspective views of detail of the shield in FIG. 2 showing an alternative embodiment.

FIG. 2D is a view of section B—B of FIG. 2.

FIGS. 2E–2F are partial cutaway perspective views of detail of the frame in FIG. 2.

DETAILED DESCRIPTION OF THE PREFERRED EMBODIMENT

Figure 1:
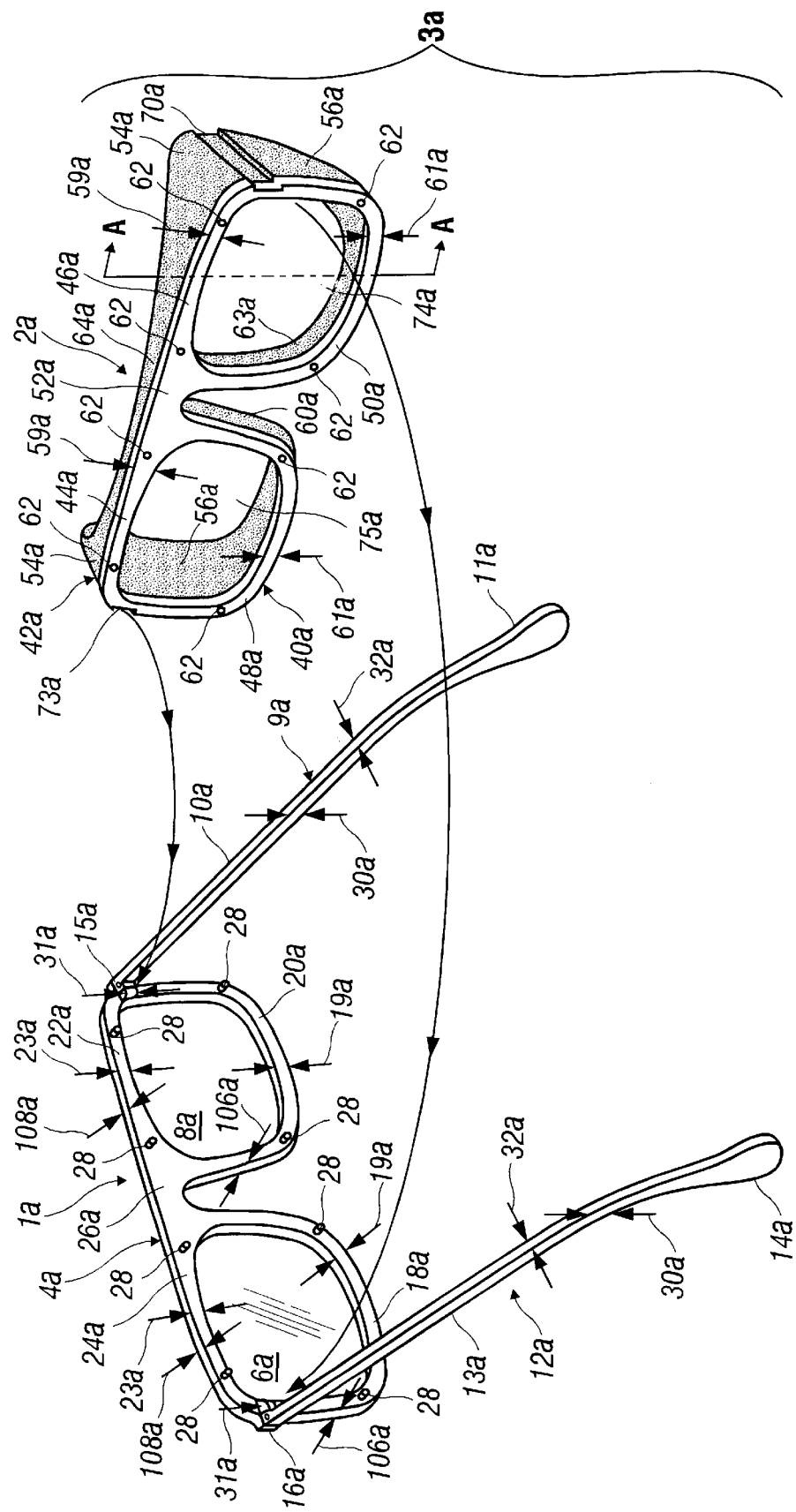
FIG. 1 is a perspective view of a first embodiment of the eye shielding system using a pin-hole retainer system, showing the eyeglasses and the detachable shield.

Referring now to the accompanying figures and in particular to FIG. 1, an eye shielding system 3a comprising two different parts, the first of which is a pair of eyeglasses (or eye goggles) 1a, and the second a detachable shield 2a, which when mounted to eyeglasses 1a function together with it as a protective eye shield. Eyeglasses 1a are formed of the frame 4a and the temple connectors 9a and 12a. While standard temple connectors are shown it is understood that the temple connectors may be of various shapes and may extend around the head of a user and may be adjustable. Any of these types of temple connectors that hold and retain the eyeglasses or eye goggles on a user's head are acceptable. Frame 4a includes left and right upper frame pieces 24a and 22a, and left and right lower frame pieces 18a and 20a. Right frame pieces 20a and 22a are joined at their respective inner and outer ends, the outer ends joining at a position proximate to the right hinge 15a, and the inner ends joining at a position proximate to the position of the cross piece 26a. Right frame pieces 20a and 22a have widths 19a and 23a respectively, of which 23a varies from proximal to distal end, and thicknesses 106a and 108a respectively. So formed, the right frame pieces serve to enclose and retain in position right lens 8a, which may or may not be a prescription lens.

Similarly on the left side of frame 4a, there are lower and upper left frame pieces 18a and 24a, having widths 19a and 23a respectively, of which 23a varies from proximal to distal end, and thicknesses 106a and 108a respectively. Left frame pieces 18a and 24a are similarly joined at their ends proximate to left hinge 16a and cross piece 26a. So formed, the left side of frame 4a encloses and retains left lens 6a. Eyeglasses 1a also comprise temple connectors 9a and 12a, right temple connector 9a being formed of right extender 10a and right earpiece 11a. Right extender piece 10a has a width 30a and depth 32a, and is joined at its proximal end to right hinge 15a which serves to join it to frame 4a. The juncture of right extender 10a and right hinge 15a has a height 31a. Similarly, left temple connector 12a has a left extender 13a and a left earpiece 14a, extender 13a having a width 30a and depth 32a, and joining frame 4a at left hinge 16a, which juncture has a height 31a.

Figure 1C:
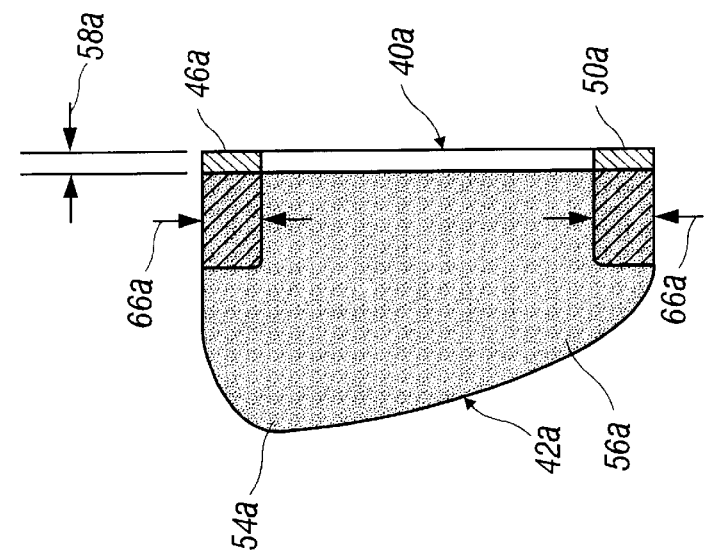
FIG. 1C is a view of section A—A of FIG. 1.
Figure 1B:
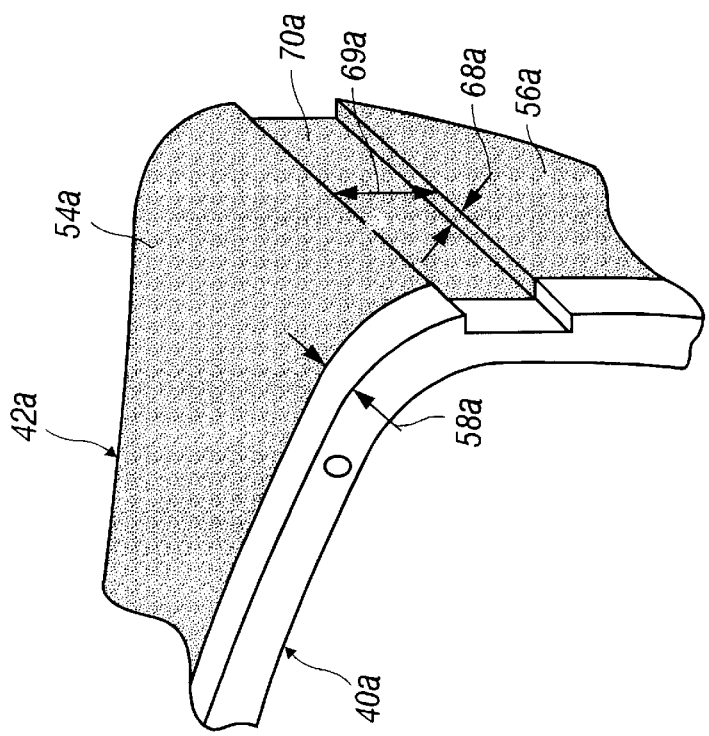
FIG. 1B is a perspective view of detail of a groove in the shield in FIG. 1.
Figure 1A:
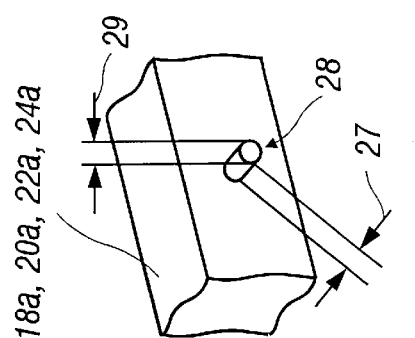
FIG. 1A is a perspective view of detail of a pin in the shield in FIG. 1.

One structure for retaining shield 2a to frame 4a is the use of a pin-hole interface. Spaced about the inner surface of frame 4a, that is the portion of the eyeglasses or goggles closest to the face, are small pins 28 that extend rearwardly from the surface of frame pieces 18a, 20a, 22a, 24a. Said pins 28 are made of a material which is capable of being rigid and being held to high tolerance, and preferably are made of some steel alloy. Referring to FIG. 1A it can be seen that pin 28 extends above the surface of frame pieces 18a, 20a, 22a, 24a for a height 27, and has a diameter 29.

Shield 2a has a substantially rigid member 40a that is capable of holding relatively high tolerances for a small hole. In one embodiment, substantially rigid member 40a is made of a resilient heavy silicone rubber. Substantially rigid member 40a, having a depth 58a (shown in FIGS. 1B and 1C) includes right and left upper rigid elements 44a and 46a, whose width 59a varies from proximal to distal end, and right and left lower rigid elements 48a and 50a, having a width 61a. Widths 59a and 61a correspond approximately to frame piece widths 23a and 19a respectively. Right rigid elements 44a and 48a are joined at their inner and outer ends, the inner ends joined proximate to rigid joining element 52a, and their outer ends proximate to right notch 73a, which is at a position spaced from rigid joining element 52a. Right rigid elements 44a and 48a are otherwise spaced apart so as to define a right lens opening 75a. Left rigid elements 46a and 50a are joined together at their inner and outer ends, the inner ends joined proximate to the rigid joining element 52a and their outer ends proximate to left notch 70a, which is at a position spaced from rigid joining element 52a. Left rigid joining elements 46a and 50a are otherwise spaced apart so as to define a left lens opening 74a. Substantially rigid member 40a is capable of conforming itself to frame 4a to seal thereto.

Shielding element 42a is permanently affixed to substantially rigid member 40a, preferably using a permanent adhesive. In the preferred embodiment, shielding element 42a is constructed of an open-cell foam that allows passage of air, but resists the passage of solid or liquid matter. Shielding element 42a may be formed by conventional methods known to those of ordinary skill. Preferably, the forward portion of shielding element 42a abuts the rear side of substantially rigid member 40a, but does not cover right and left lens openings 74a and 75a. Shielding element 42a extends rearwardly from substantially rigid member 40a and has a thickness 66a, seen in FIG. 1C. Returning to FIG. 1, shielding element 42a extends rearwardly a greater distance proximate to grooves 70a and 73a, and near regions 54a and 56a, while extending rearwardly a lesser distance adjacent to rigid joining element 52a and regions 60a, 63a and 64a. Shielding element 42a is conformable and extends rearward sufficiently to seal to a wearer's face. Grooves 70a and 73a extend rearwardly from the face of substantially rigid member 40a to the rear portion of shielding element 42a. As shown in FIG. 1B, groove 70a has a width 69a, and a depth 68a. Detail of groove 70a in FIG. 1B is typical of groove 73a. Widths and depths 69a and 68a correspond approximately to width and depth 30a and 32a of extender pieces 10a, 13a, or of the corresponding portion of temple connectors 9a, 12a if in a different configuration.

Holes 62 are spaced about the substantially rigid member 40a in positions corresponding with the positions of pins 28 on frame 4a, which when fitted together permit the lens openings 74a and 75a to correspond to left and right lenses 6a and 8a. Holes 62 have a depth greater than height 27, shown in FIG. 1A, of pins 28. The diameter of holes 62 corresponds to diameter 29 of pins 28. This permits holes 62 to engage pins 28, and for the resilient material of substantially rigid member 40a surrounding holes 62 to grip pins 28, and thus retain shield 2a to frame 4a.

Shield 2a may be attached to eyeglasses 1a by placing substantially rigid member 40a of shield 2a against frame 4a and aligning holes 62 with pins 28. Once aligned thereto, shield 2 may be pressed forward onto the rear side of frame 4a until holes 62 engage pins 28 and a snug fit is achieved. Shield 2a is detachable simply by pulling rearwardly, which may first be done at one end, disengaging holes 62 from pins 28. Shield 2a may then be discarded.

Figure 2:
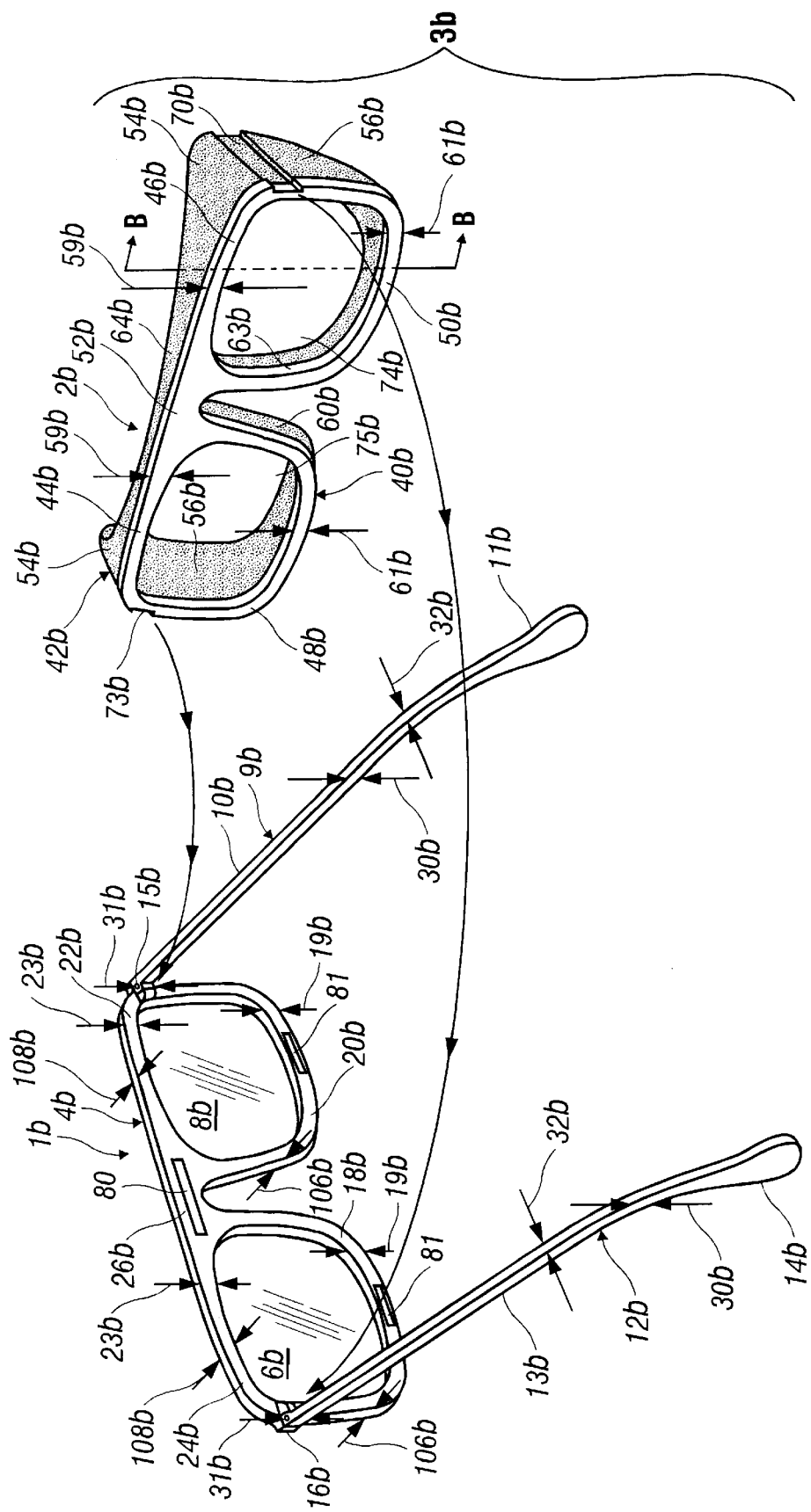
FIG. 2 is perspective view of a second embodiment of the eye shielding system using a magnetic retainer system, showing the eyeglasses and the detachable shield.

Referring to FIG. 2, a second embodiment is shown which includes eyeglasses (or eye goggles) 1b and detachable shield 2b. Components which are similar to those of the embodiment shown in previous figures, generally 3a in FIG. 1A, bear the same numerals but are succeeded by the letter "b". Components bearing the same numeral can be understood to share similar relationships and structure. Eyeglasses 1b include frame 4b, the right upper and lower frame pieces 22b, 20b, and the left upper and lower frame pieces 24b, 18b, the left and right pieces joined at their inner ends near crosspiece 26b and at their outer ends near left and right hinges 16b, 15b. Lower frame pieces have width 19b and thickness 106b, and upper frame pieces width 23b and thickness 108b. Eyeglasses 1b also include right and left lenses 8b and 6b, and right and left temple connectors 9b and 12b, having width 30b and depth 32b. Right temple connector 9b includes right extender 10b, and earpiece 11b, while left temple connector 12b includes corresponding pieces 13b, 14b. Eyeglasses 1b further include left and right hinges 16b, 1b, which have a height 31b. As with the first embodiment, it is understood that the temple connectors 9b and 12b may take various configurations.

The embodiment shown in FIG. 2 differs by the use of magnets 80 which, in the one embodiment, are located within or adjacent to crosspiece 26b, and within the left and right lower frame pieces, 18b, 20b.

Shield 2b is substantially similar to shield 2a shown in FIG. 1, having a substantially rigid member 40b, which includes right upper and lower rigid elements 44b, 48b, and left upper and lower rigid elements 46b, 50b, and rigid joining element 52b. Substantially rigid member 40b has a depth 58b (shown in FIGS. 2A and 2D); upper rigid elements 44b and 46b have width 59b which varies from the proximal to distal ends, and lower rigid elements have width 61b. Widths 59b and 61b correspond approximately to frame piece widths 23b, 19b. Shield 2b also includes shielding element 42b preferably permanently affixed to substantially rigid number 40b using an adhesive, shielding element 42b having a thickness 66b, seen in FIG. 2D. Returning to FIG. 2, shielding element 42b extends rearwardly a greater distance proximate to grooves 70b and 73b, and near regions 54b and 56b, while extending rearwardly a lesser distance adjacent to rigid joining element 52b and regions 60b, 63b and 64b. Shielding element 42b extends rearward sufficiently, and is comfortable to, seal against a wearer's face. Shield 2b similarly has left and right grooves 70b, 73b, and lens openings 74b, 75b. Detail of groove 70b shown in FIG. 2A is typical of groove 73b.

In one form of the embodiment shown in FIG. 2, all of substantially rigid member 40b, is ferrous and attracted to upper magnet 80 and lower magnets 81, in frame 4b. As shown in FIGS. 2E and 2F, upper magnet 80 has a length 110, width 112 and thickness 114. Lower magnets 81 have a length 116, width 118 and thickness 120. Width 118 is less than or equal to frame piece width 19b. Similarly thicknesses 114 and 120 are less than or equal to frame piece thicknesses 108b and 106b respectively.

In a second, alternative embodiment, shown in detail in FIGS. 2B and 2C, substantially rigid member 40b is not ferrous, but located rearward of and preferably adjacent to right and left lower rigid elements 48b, 50b, and rigid joining element 52b, are upper magnetic attracter 83 and lower magnetic attracters 82. Magnetic attracters 82, 83 may be either a ferrous metal attracted to magnets 80, or a magnet. Attracter faces 84 are preferably affixed directly to the rearward side of rigid elements 48b, 50b, 52b of substantially rigid member 40b. Magnetic attracters 82, 83 are placed on the rearward side of substantially rigid member 40b in positions approximately corresponding to the positions of magnets 80, 81 on frame 4b. Shielding element 42b is affixed and sealed to the rearward side of magnetic attracter 82 using an adhesive. Upper magnet 83 has a length 122, width 124 and thickness 126. Lower magnets 82 have length 128, width 130 and thickness 132. Width 130 is less than or equal to frame piece width 61b. Thicknesses 132 and 126 are less than thickness 66b of shielding element 42b.

Shield 2b may be attached to eyeglasses 1b by aligning substantially rigid member 40b with frame 4b, so that lens openings 74b, 75b are aligned with lenses 6b, 8b respectively. In the embodiment shown in FIG. 2, a ferrous substantially rigid member 40b approaches upper and lower magnets 80, 81 in frame 4b, the magnetic attraction therebetween draws and holds shield 2b and eyeglasses 1b together and creates a snug fit. To detach shield 2b, either substantially rigid member 40b or shielding element 42b may be pulled rearwardly from eyeglasses 1b, until the magnetic attraction is no longer operative. Shield 2b may then be discarded. In the alternative embodiment shown in FIGS. 2B and 2C, the process is similar, except that the magnetic attraction is between magnets 80, 81 and magnetic attracters 82, 83.

Figure 3:
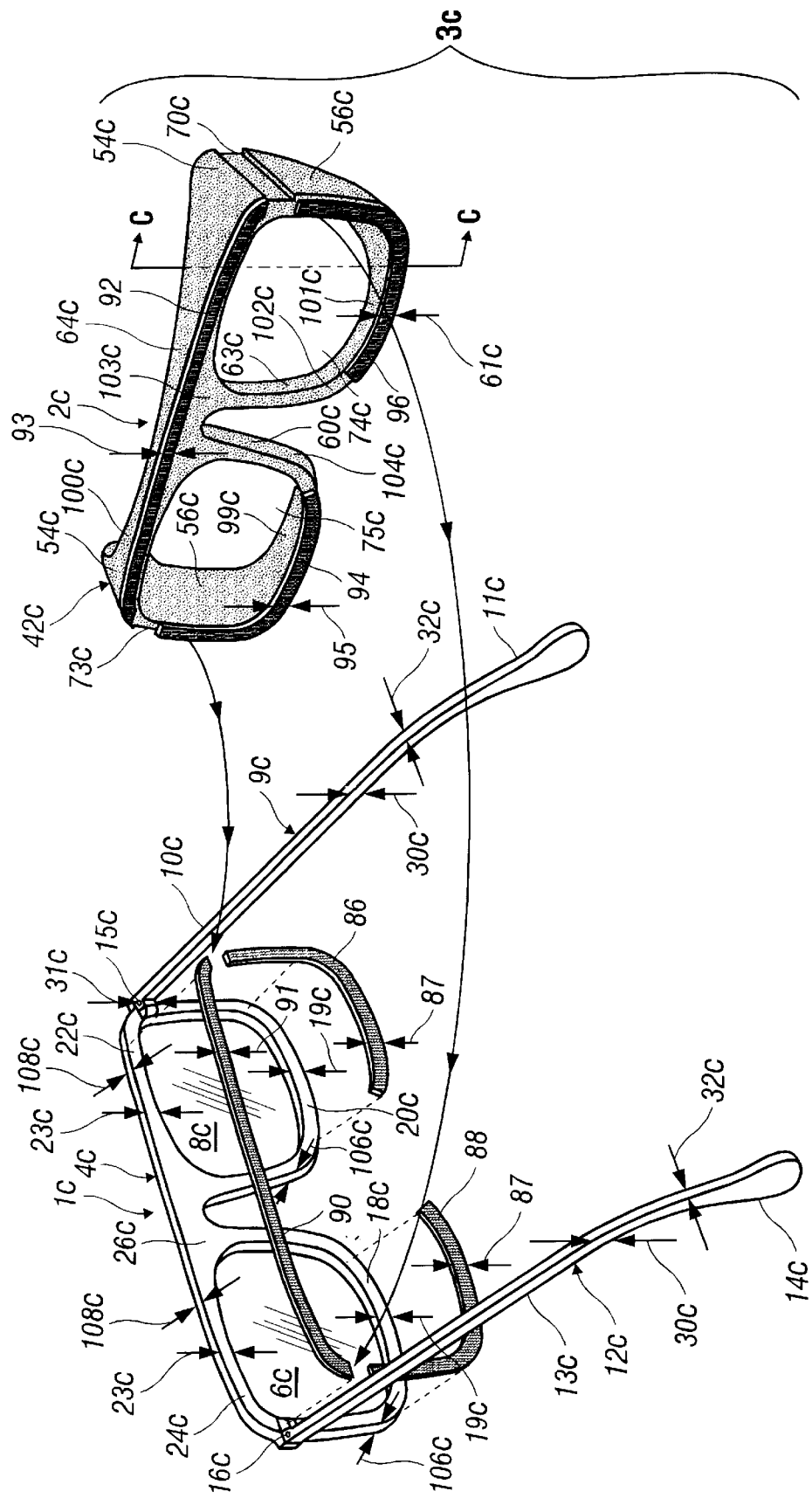
FIG. 3 is perspective view of a third embodiment of the eye shielding system using a hook and loop fastener retainer system, showing the eyeglasses and the detachable shield.

The further embodiment of an eye protection system 3c is depicted in FIG. 3, including a pair of eyeglasses (or eye goggles) 1c and a shield 2c. In this embodiment, elements that are substantially the same and perform the same functions as in previous figures, generally 3a and 3b in FIGS. 1 and 2, utilize the letter "c" and the appropriate numeral. Eyeglasses 1c include frame 4c, the right upper and lower frame pieces 22c, 20c, and the left upper and lower frame pieces 24c, 18c. Lower frame pieces have width 19c and thickness 106c and upper frame pieces width 23c and thickness 108c. Eyeglasses 1c also include right and left lens 8c and 6c, and right and left temple connectors 9c and 12c, having width 30c and depth 32c. Right temple connector 9c includes right extender 10c, and earpiece 11c, while left temple connector 12c includes corresponding pieces 13c, 14c. Eyeglasses 1c further include left and right hinges 16c, 15c, which have a height 31c. As with the first and second embodiments, it is understood that temple connectors 9c and 12c may take various configurations.

Eyeglasses 1c also includes three pieces of hook and loop fastener, upper fastener 90, and left and right lower fasteners 88, 86. Upper fastener 90 extends approximately from right hinge 15c to left hinge 16c, and has a width 91 approximately equal to the width of the upper frame pieces 23c. The forward side of upper fastener 90 is affixed to frame 4c, preferably using adhesive, as are lower fasteners 86 and 88. Lower right fastener 86 has a width 87 which is approximately equal to lower frame piece width 19c, and extends from below hinge 15c along the greater part of lower frame piece 20c, and may optionally continue until it reaches upper fastener 90. Lower left fastener 88 has width 87, and extends from left hinge 16c across lower left frame piece 18c in a similar fashion.

Figure 3B:
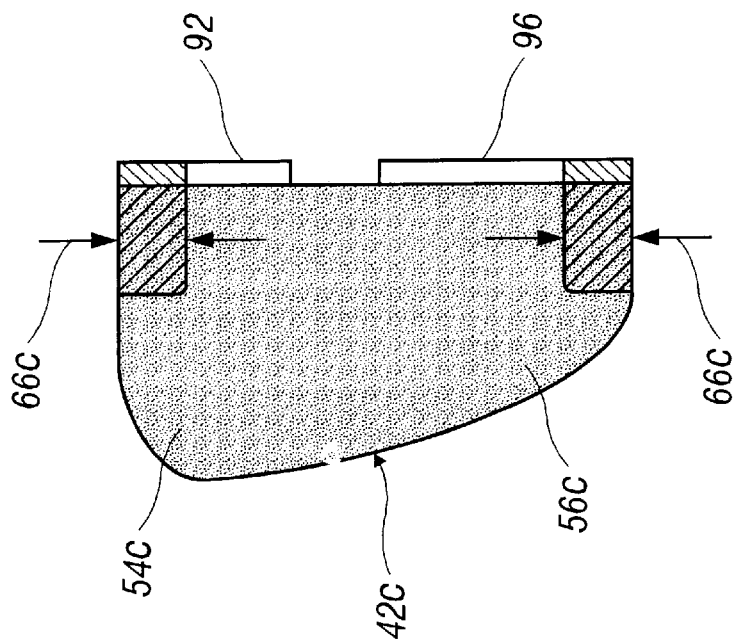
FIG. 3B is a view of section C—C of FIG. 3.
Figure 3A:
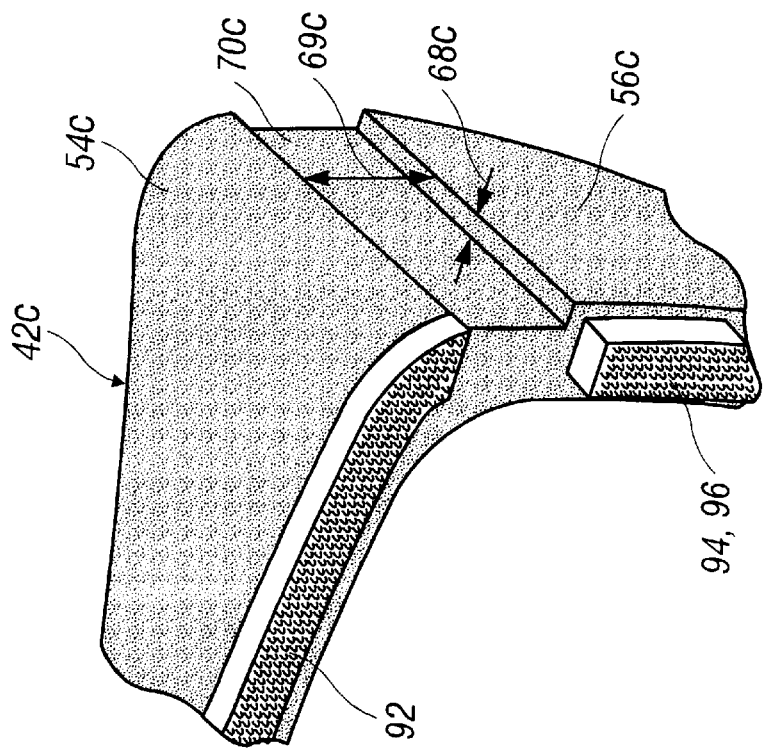
FIG. 3A is a perspective view of detail of a groove in the shield in FIG. 3.

Shield 2c shares many of the same elements as shields 2a and 2b. It has a shielding element 42c, having a thickness 66c, seen in FIG. 3B. Returning to FIG. 3, shielding element 42c has an upper shield element 100c, right and left lower shield elements 104c and 102c, and a bridging element 103c. Lower shield elements 102 and 104c are spaced from upper shield element 100c, and thereby define left and right lens opening 74c, 75c. Similar to those in FIGS. 1 and 2, shield element 42c extends farther rearwardly in regions 56c and 54c, and proximate to grooves 70c, 73c than in regions 60c, 63c, 64c, 99c, or 101c. Shielding element 42c extends rearward sufficiently to, and is comfortable to, seal against a wearer's face. Shown in FIG. 3B, in section, is thickness 66c of shielding element 42c. Also similar to the shield elements in FIGS. 1 and 2, shield element 42c has left and right grooves, 70c, 73c, which extend from front to rear. Referring to FIG. 3A, said groove 70c has width 69c, and depth 68c. Detail of groove 70c in FIG. 3A is typical of groove 73c.

Returning to FIG. 3, shield 2c further comprises upper shield fastener 92 and lower left and right shield fasteners, 96 and 94. Shield fasteners 92, 94, 96 are also hook and loop fabric and mate with opposed fabric comprising fasteners 86, 88, 90 attached to frame 4c. Shield fasteners 92, 94, 96 abut the front of shielding element 42c. Upper shield fastener 92 has width 93; lower right and left shield fasteners 94, 96 each have width 95. Upper shield fastener 92 extends approximately from left groove 70c to right groove 73c and width 93 is approximately equal to width 91 of the upper fastener 90 attached to frame 4c and to upper shield element 100c. Upper shield fastener 92 is attached to upper shield element 100c, preferably using a permanent adhesive. Lower shield fasteners 94 and 96 are similarly affixed to left and right lower shield elements 102c and 104c. Right lower shield fastener 94 extends approximately from below right groove 73c along lower shield element 104c and the bottom of right lens opening 75c, and may or may not reach bridging element 103c of shielding element 42c. Left lower shield fastener 96 is attached in a similar fashion to left lower shield element 102c. The positions of shield fasteners 92, 94, 96 preferentially correspond to those of fasteners 86, 88 and 90. Width 95 of lower shield fasteners 94 and 96 are approximately equal to width 87 of lower fasteners 86 and 88 attached to frame 4c and to lower shield elements 104c and 102c. When shield fasteners 92, 94, 96 are properly affixed to frame fasteners 86, 88, 90, which are attached to frame 4c, lens openings 74c and 75c permit the wearer to see through the openings in shielding element 42c and through lenses 6c, 8c.

Shield 2c may be attached to eyeglasses 1c by aligning upper fastener 91 and upper shield fastener 92, and lower fasteners 86, 88 and lower shield fasteners 94, 96, and pressing those fasteners 91, 86, 88 attached to frame 4c to those fasteners, 92, 94, 96, attached to shielding element 42c. The hook and loop fabric of the fasteners would then engage, retaining shield 2c to eyeglasses 1c and permitting a snug fit. Shield 2c may be detached from eyeglasses 1c by pulling gently rearwardly on shielding element 42c to disengage the hook and loop fabric of the fasteners. Shield 2c may then be discarded.

Figure 4:
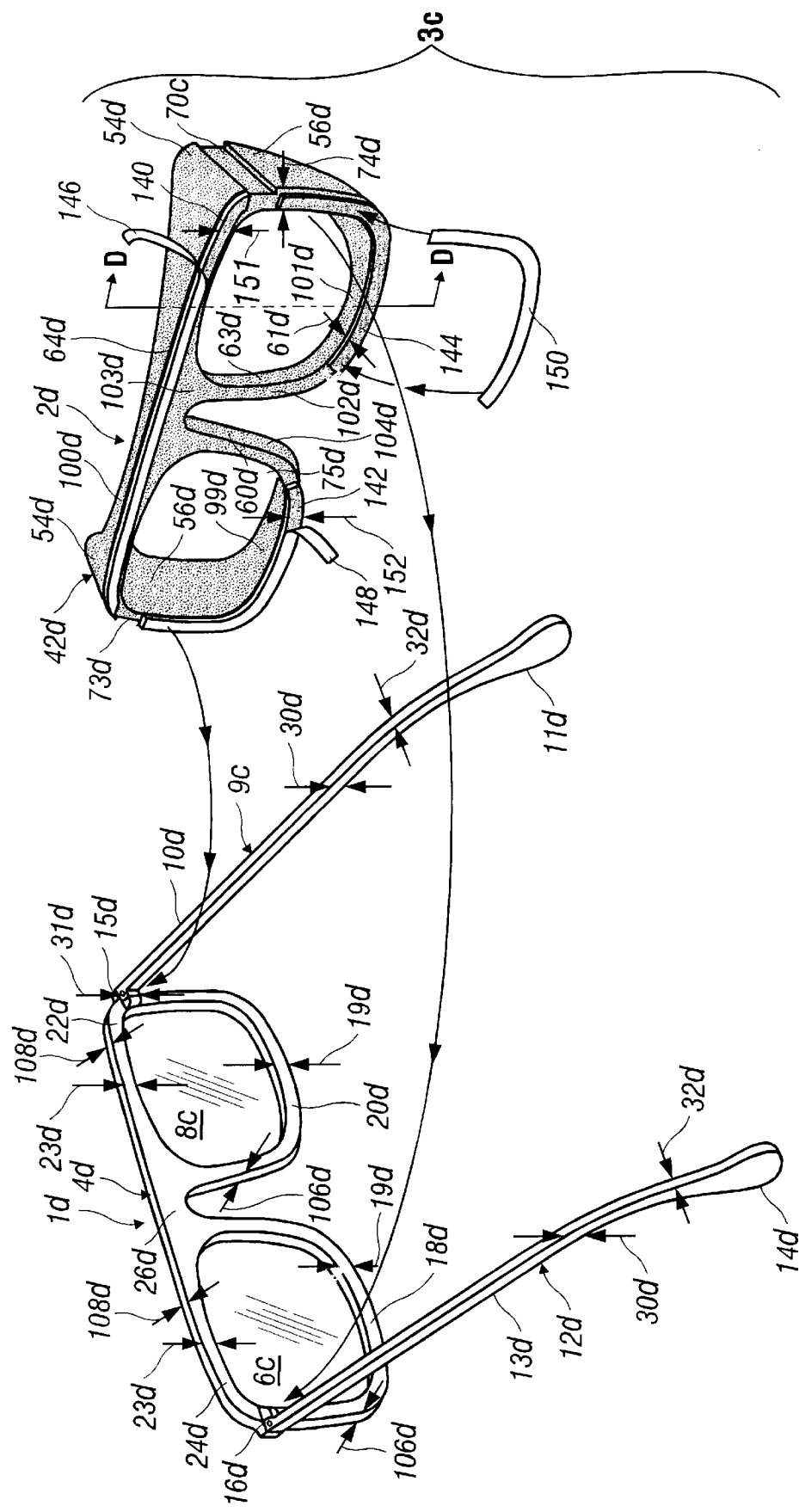
FIG. 4 is perspective view of a fourth embodiment of the eye shielding system using an adhesive layer retainer system, showing the eyeglasses and the detachable shield.

A further embodiment of an eye protection system 3d is depicted in FIG. 4, including a pair of eyeglasses (or eye goggles) 1d and a shield 2d. In this embodiment, elements that are substantially the same and perform the same functions as in previous figures, generally 3a, 3b and 3c in FIGS. 1, 2 and 3, utilize the letter "d" and the appropriate numeral. Eyeglasses 1d include frame 4d, right upper and lower frame pieces 22d, 20d, and left upper and lower frame pieces 24d, 18d. Lower frame pieces have width 19d and thickness 106d and upper frame pieces width 23d and thickness 108d. Eyeglasses 1d also include right and left lens 8d and 6d, crosspiece 26d, and right and left temple connectors 9d and 12d, having width 30d and depth 32d. Right temple connector 9d includes right extender 10d, and earpiece 11d, while left temple connector 12d includes corresponding pieces 13d, 14d. Eyeglasses 1d further include left and right hinges 16d, 15d, which have a height 31d. As with the first and second embodiments, it is understood that temple connectors 9d and 12d may take various configurations.

Figure 4B:
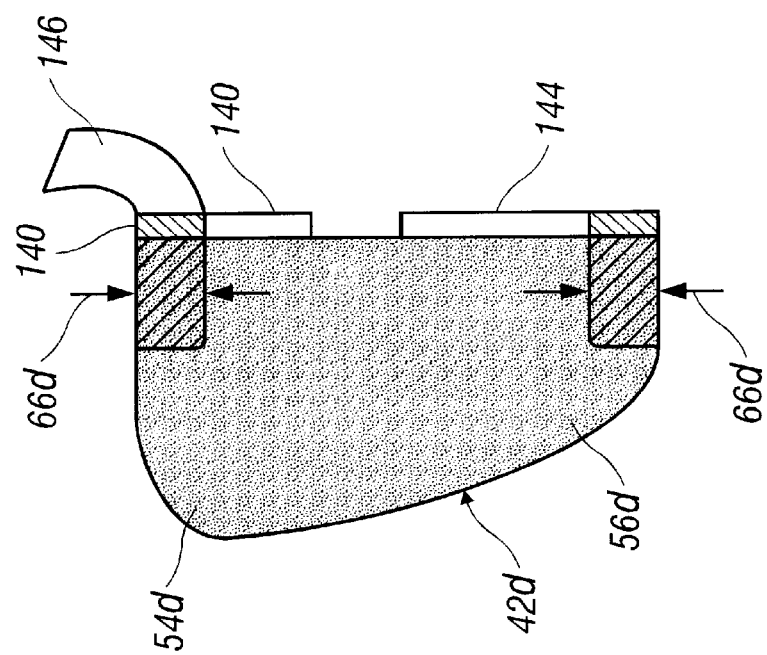
FIG. 4B is a view of section D—D of FIG. 4.
Figure 4A:
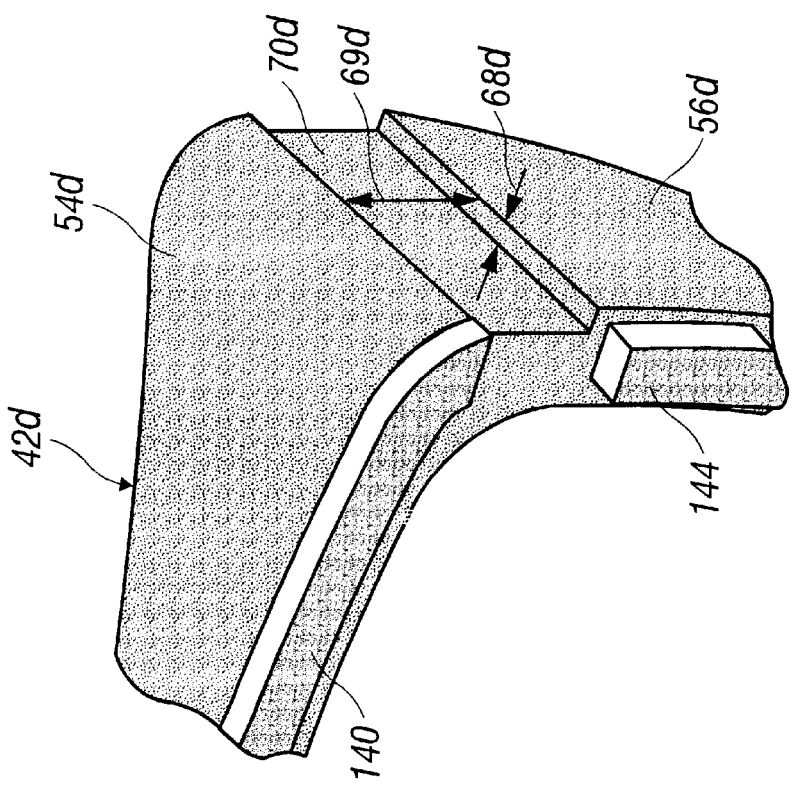
FIG. 4A is a perspective view of detail of a groove in the shield in FIG. 4.

Shield 2d shares many of the same elements as shields 2a and 2b and particularly so with respect to shield 2c, seen in FIGS. 1, 2 and 3. It has a shielding element 42d, having a thickness 66d seen in FIG. 4B. Returning to FIG. 4, shielding element 42d has an upper shield element 100d, right and left lower shield elements 104d and 102d, and a bridging element 103d. Lower shield elements 102d and 104d are spaced from upper shield element 100d, and thereby define left and right lens opening 74d, 75d. Shield elements 100d, 102d and 104d and lens openings 74d, 75d are in this way conformed to the elements of frame 4d. Similar to those in FIGS. 1, 2 and 3, shield element 42d extends farther rearwardly in regions 56d and 54d, and proximate to grooves 70d, 73d than in regions 60d, 63d, 64d, 99d, or 101d. Shielding element 42d extends sufficiently rearward to, and is comfortable to, seal against a wearer's face. Shown in FIG. 4B, in section, is thickness 66d of shielding element 42d. Also similar to the shield elements in FIGS. 1, 2 and 3, shield element 42d has left and right grooves, 70d, 73d, which extend from front to rear. Referring to FIG. 4A, said groove 70d has width 69d, and depth 68d. Detail of groove 70d in FIG. 4A is typical of groove 73d.

Returning to FIG. 4, on the front of shielding element 42d, are adhesive strip 140, having width 151, and lower right and left adhesive strips 142, 144 each having width 152. Adhesive strips 140, 142, 144 are a pressure-sensitive adhesive layer which comprise a portion of the front surface of shielding element 42d. This adhesive layer has adhesive qualities on both sides. In one embodiment, upper adhesive strip 140 may be formed by applying a resilient adhesive material to shield element 42d on frontal surface of upper shield element 100d. Lower adhesive strips 142, 144 are similarly formed by adhesive material applied to the frontal surfaces of right and left lower shield elements 104d and 102d. However, a pressure-sensitive double-sided tape may also be applied to shield elements 104d, 102d in place of adhesive material applied directly thereto. Upper adhesive strip 140 and lower left and right adhesive strips 144, 142 are covered prior to use by upper peel strip 146, and lower left and right peel strips 150, 148 respectively. Peel strips 146, 148, 150 are a paper or paper-like strip that adheres to and protects the normally tacky surface of adhesive strips 140, 142, 144, and may perform the same function for an embodiment using double-sided tape. Upper adhesive strip 140 extends approximately from left groove 70d to right groove 73d and width 151 is approximately equal in width 23d of upper frame pieces 22d, 24d and may be approximately equal width of upper shield element 100d. Right lower adhesive strip 142 extends approximately from below right groove 73d along lower shield element 104d and the bottom of right lens opening 75d, and may or may not reach bridging element 103d of shielding element 42d. Left lower tape fastener 144 is attached in a similar fashion to left lower shield element 102d. The position of upper adhesive strip 140 preferentially corresponds closely to the location of upper frame pieces 22d, 24d and crosspiece 26d. Similarly, lower adhesive fasteners 142, 144 preferentially correspond closely to lower frame pieces 18d, 20d. Similarly, width 152 of lower adhesive strips 142, 144 may be approximately equal to width 19d of lower frame pieces 18d, 20d and also to lower shield elements 104d and 102d. To permit shield 2d to be attached to eyeglasses 1d, upper and lower peel strips 146, 148, 150 may be removed by peeling them away from adhesive strips 140, 142, 144 at their common ends. This is also shown in more detail in FIG. 4A. Peel strips 146, 148, 150 may then be discarded, and shield openings 74d, 75d aligned with lenses 6d, 8d. Then, adhesive strips 140, 142, 144 may be applied to frame 4d by pressing their adhesive surface to the rear side of frame 4d, until a snug fit is achieved. When tape fasteners 140, 142, 144 are properly affixed to frame 4d, lens openings 74d and 75d permit the wearer to see through the openings in shielding element 42d and through lenses 6d, 8d. Shield 2d is removable from eyeglasses 1d by pulling shield 2d rearwardly, separating frame 4d from adhesive tapes 140, 142, 144. Shield 2d may then be discarded.

The invention claimed is:

1. An eye shield system for a wearer's face, comprising:
an eyeglass frame having left and right ends, a rearward side and two lenses;
left and right connectors joined to the left and right ends of the frame;
a shield, comprising an air-permeable material, having left and right ends, and forward and rearward sides, wherein the air-permeable material allows passage of gasses, but blocks passage of liquids and solids, and the shield has two lens openings formed therein;
wherein said shield's forward side abuts the frame's rearward side and said shield's rearward side contacts the face of the wearer of the frame to seal with the wearer's face; and
a retainer releasably securing the shield's forward side to the frame's rearward side.

2. The invention of claim 1, wherein the air-permeable material comprises an open-cell foam.

3. The invention of claim 1, wherein the shield has grooves formed in the left and right ends to receive the right and left connectors.

4. The invention of claim 1, wherein the retainer comprises hook and loop fasteners.

5. The invention of claim 1, wherein the retainer comprises an adhesive layer adhered to the shield's forward surface, wherein said adhesive layer is pressure sensitive to adhere said shield to the frame's rearward side.

6. The invention of claim 5, wherein said adhesive layer is applied in a plurality of regions.

7. The invention of claim 6, wherein said retainer further comprises a removable protective strip substantially covering said adhesive areas.

8. The invention of claim 1, wherein the forward side of the shield is formed of a resilient material.

9. The invention of claim 8, wherein the retainer comprises pins attached to the frame and wherein the forward side of the shield has holes formed therein that receive the pins.

10. The invention of claim 1 wherein the forward side of the shield is formed of a substantially rigid material.

11. The invention of claim 10, wherein the retainer comprises pins attached to the frame and wherein the forward side of the shield has holes formed therein that receive the pins.

12. The invention of claim 10 wherein the substantially rigid material is magnetically attractable.

13. The invention of claim 12, wherein the retainer comprises at least one magnet affixed to the frame.

14. The invention of claim 1, wherein the retainer comprises at least one magnet affixed to the shield, the frame comprising a magnetically attractable material.

15. An eye shield system for a wearer's face, comprising:
eyeglasses comprising:
a frame, having left and right ends and a rearward side, comprising:
left upper and lower frame pieces; and
right upper and lower frame pieces, wherein the right frame pieces are functionally joined to the left frame pieces; and
left and right connectors, the left connector joined to the left end of the frame, the right connector joined to the right end of the frame, both left and right connectors extending generally rearwardly from the frame;
left and right lenses, fixed in place in the frame, the left lens by the left frame pieces and the right lens by the right frame pieces; and
a shield, having forward and rearward sides, comprising:
a shield structure, comprising an air-permeable material, having forward and rearward sides, wherein said air-permeable material allows passage of gasses, but resists passage of liquids and solids, said forward side has at least one lens opening formed therein, and said forward side is operable to be releasably secured to the rearward side of the frame; and a retainer for releasably securing the shield structure's forward side to the frame's rearward side.

16. The invention of claim 15, wherein the shield structure is resilient and extends rearwardly to form a seal with the wearer's face.

17. The invention of claim 15 wherein the air-permeable material comprises an open-cell foam.

18. The invention of claim 15, wherein the shield structure further comprises a substantially rigid member, having forward and rearward sides, wherein said forward side is operable to be releasably secured to the frame's rearward side, and the air-permeable material is affixed to said rearward side.

19. The invention of claim 18, wherein the retainer comprises a plurality of magnets affixed to the frame, and wherein the substantially rigid member is metal.

20. The invention of claim 18, wherein the retainer comprises a plurality of pins projecting from the substantially rigid member, wherein the substantially rigid member is plastic, a plurality of holes are formed to penetrate the frame, and said holes are operable to releasably engage the pins.

21. The invention of claim 18, wherein the retainer comprises a plurality of pins projecting from the frame, wherein a plurality of holes are formed to penetrate the substantially rigid member, and said holes are operable to releasably engage the pins.

22. The invention of claim 21, wherein the pins are metal and the substantially rigid member is plastic.

23. The invention of claim 21, wherein the pins are metal and the substantially rigid member is formed of a resilient material.

24. The invention of claim 15, wherein the shield further comprises a magnetically attractable material, and the retainer comprising a plurality of magnets affixed to the frame.

25. The invention of claim 15, wherein the frame comprises a magnetically attractable material, and the retainer comprising a plurality of magnets.

26. The invention of claim 15, wherein the retainer comprises hook and loop fasteners affixed to the frame's rearward side and the shield's forward side.

27. The invention of claim 15, wherein the retainer comprises an adhesive layer on the shield's forward side, wherein said adhesive layer is operable to adhere the shield to the frame's rearward side.

28. The invention of claim 27, wherein the adhesive layer is applied on a plurality of strips on the shield's forward side.

29. The invention of claim 28, wherein the retainer further comprises a plurality of removable strips, wherein said removable strips overly the strips of adhesive layer, and said removable strips are peelingly disengageable from the adhesive layer.

30. An eye shield system for a wearer's face, comprising:
eyeglasses having:
a frame, having left and right ends and a rearward side, including:
left upper and lower frame pieces, each having proximal and distal ends, the left upper frame piece proximal end joined to the left lower frame piece proximal end, the left upper frame piece distal end joined to the left lower frame piece distal end;
right upper and lower frame pieces, each having proximal and distal ends, the right upper frame piece proximal end joined to the right lower frame piece proximal end, the right upper frame piece distal end joined to the right lower frame piece distal end; and
at least one crosspiece, having left and right ends, the crosspiece functionally joining the left proximal frame piece ends to the right proximal frame piece ends;
left and right lenses, fixed in place in the frame, the left lens by the left frame pieces and the right lens by the right frame pieces; and
left and right connectors, having proximal and distal ends, the left connector proximal end joined to the left end of the frame, the right connector proximal end joined to the right end of the frame, both connectors extending generally rearwardly from the frame;
a shield, comprising:
left and right ends and forward and rearward sides;
a substantially rigid member, having left and right ends and a forward and rearward side, wherein the forward side is operable to be releasably secured to the frame's rearward side;
a shielding element, having left and right ends and forward and rearward sides, said forward side affixed to the rearward side of the substantially rigid member, said rearward side extending rearwardly from the substantially rigid member a distance greater at the left and right ends to form a seal with the wearer's face, the shielding element having a thickness, and comprising an open-cell foam; and
a retainer releasably securing the forward side of the shield to the rearward side of the frame;
wherein said shield has grooves formed on the ends to receive and retain the left and right connectors.

31. The invention of claim 30, wherein the retainer comprises a plurality of pins, distributed about the substantially rigid member, and projecting forwardly from the substantially rigid member, wherein a plurality of holes are formed in the frame pieces, in a number at least equal to, and overlying, the pins distributed about the upper and lower frame pieces, and said holes are operable to releasably secure the pins.

32. The invention of claim 30, wherein the retainer comprises a plurality of pins, distributed about the upper and lower frame pieces, and projecting rearwardly from the frame pieces, wherein a plurality of holes are formed in the substantially rigid member, in a number at least equal to, and overlying, the pins distributed about the substantially rigid member, and said holes are operable to releasably secure the pins.

33. The invention of claim 32, wherein the pins are metal and the substantially rigid member is plastic.

34. The invention of claim 30, wherein the shield further comprises a magnetically attractable metal, the retainer comprising a plurality of magnets affixed to the frame.

35. The invention of claim 34, wherein the magnets are embedded within the frame, and the substantially rigid member is the magnetically attractable metal.

36. The invention of claim 30, wherein the frame pieces comprise a magnetically attractable metal, the retainer comprising a plurality of magnets affixed to the substantially rigid member.

37. The invention of claim 30, wherein the retainer comprises hook and loop fasteners affixed to the rear side of the frame and the forward side of the shield.

38. The invention of claim 30, wherein the retainer comprises an adhesive layer on a plurality of areas on the forward surface of the substantially rigid member, wherein said adhesive layer is operable to adhere the shield to the rearward side of the frame.

39. The invention of claim 38, wherein the retainer further comprises a plurality of removable strips, wherein said removable strips cover said adhesive layers.

40. An eye shield system for a wearer's face, said system comprising:

a pair of eyeglasses having at least one lens incorporated therein;

a shield coupled to said pair of eyeglasses, said shield comprising an air-permeable material that blocks the passage of solids and liquids therethrough;

said shield having forward and rearward edges, said forward edge being sealingly engaged to a rearward side of said pair of eyeglasses and said rearward edge arranged for sealing contact with a wearer's face; and said shield further comprising at least one lens opening formed therein, said at least one lens opening being positioned about said at least one lense of said pair of eyeglasses.

41. The invention of claim 40 further comprising:

said at least one lens comprises two lenses;

said at least one lens opening comprises two lens openings; and each of said two lens openings is positioned about one of said two lenses.

42. A shield to be utilized in conjunction with a pair of eyeglasses, said shield comprising:

a unitary body configured to fit interstitially between a pair of eyeglasses and a wearer's face, said unitary body comprising an air-permeable material that blocks the passage of solids and liquids therethrough;

said shield having forward and rearward edges, said forward edge being adapted for releasable engagement upon a rearward side of a pair of eyeglasses and said rearward edge adapted to engage with a wearer's face and prevent the passage of solid and liquids therebetween; and said shield further comprising at least one lens opening formed therein, said at least one lens opening being configured to be positioned about a lense of a pair of eyeglasses.

43. The invention of claim 42 further comprising:

at least one groove recessed into said unitary body for receivingly engaging an ear piece of an eyeglass frame for releasably fixing said unitary body relative to the eyeglass frame.

44. The invention of claim 43 further comprising:

said at least one groove extending from said forward edge to said rearward edge of said shield, said at least one grove being open ended at each of said forward and rearward edges of said shield.

45. The invention of claim 42 further comprising:

a plurality of receiving apertures extending into a forward surface of said shield, each of said plurality of receiving apertures configured to receivingly engage mating grip pins located on a pair of eyeglasses for releasably fixing said unitary body relative to the eyeglass frame.

46. The invention of claim 45 further comprising:

a substantially rigid member located at said forward surface of said shield and into which said plurality of receiving apertures extend, said substantially rigid member being joined to a conformable member of said shield located rearwardly thereto.

* * * * *